(12) United States Patent
Fukada

(10) Patent No.: US 8,457,732 B2
(45) Date of Patent: Jun. 4, 2013

(54) BIOMETRIC APPARATUS

(75) Inventor: Kosei Fukada, Tokyo (JP)

(73) Assignee: Tanita Corporation, Tokyo (JP)

( * ) Notice: Subject to any disclaimer, the term of this patent is extended or adjusted under 35 U.S.C. 154(b) by 935 days.

(21) Appl. No.: 12/149,918

(22) Filed: May 9, 2008

(65) Prior Publication Data

US 2008/0281222 A1 Nov. 13, 2008

(30) Foreign Application Priority Data

May 9, 2007 (JP) ................................. 2007-124688

(51) Int. Cl.
*A61B 5/05* (2006.01)

(52) U.S. Cl.
USPC ...... 600/547; 600/587; 177/25.13; 177/25.17

(58) Field of Classification Search
USPC ............... 600/300–301, 547, 593; 177/25.13, 177/27.17, 177; 345/473; 702/173; 705/414; 715/709
See application file for complete search history.

(56) References Cited

U.S. PATENT DOCUMENTS

| | | | |
|---|---|---|---|
| 4,301,879 A * | 11/1981 | Dubow | 177/5 |
| 6,354,996 B1 * | 3/2002 | Drinan et al. | 600/300 |
| 6,583,369 B2 * | 6/2003 | Montagnino et al. | 177/177 |
| 6,591,168 B2 * | 7/2003 | Odinak et al. | 701/1 |
| 6,781,067 B2 * | 8/2004 | Montagnino et al. | 177/25.13 |
| 6,790,178 B1 * | 9/2004 | Mault et al. | 600/300 |
| 7,104,954 B2 | 9/2006 | Koyama et al. | |
| 7,186,930 B1 * | 3/2007 | Wong et al. | 177/25.13 |
| 7,193,163 B1 * | 3/2007 | Kesselman | 177/25.13 |
| 2002/0134589 A1 * | 9/2002 | Montagnino et al. | 177/25.16 |
| 2003/0090389 A1 * | 5/2003 | Maeda et al. | 340/825.72 |
| 2004/0229575 A1 | 11/2004 | Chan et al. | |
| 2004/0238228 A1 | 12/2004 | Montague et al. | |
| 2005/0185799 A1 * | 8/2005 | Bertram | 381/67 |
| 2005/0247494 A1 * | 11/2005 | Montagnino | 177/60 |
| 2006/0229557 A1 * | 10/2006 | Fathallah et al. | 604/131 |
| 2007/0068527 A1 * | 3/2007 | Baker | 128/204.23 |
| 2008/0073128 A1 * | 3/2008 | Umemoto | 177/5 |
| 2009/0204018 A1 * | 8/2009 | Tseng et al. | 600/547 |

FOREIGN PATENT DOCUMENTS

| | | |
|---|---|---|
| CN | 1470214 A | 1/2004 |
| EP | 1 288 639 A1 | 3/2003 |
| EP | 1 698 277 A1 | 9/2006 |
| JP | 10-179536 | 7/1998 |
| WO | WO 2006/136390 A1 | 12/2006 |

OTHER PUBLICATIONS

Chinese Office Action, w/ English translation thereof, issued in Chinese Patent Application No. CN 200810096142.7 dated Feb. 5, 2010.
European Search Report issued in European Patent Application No. EP 08006821.6 dated Apr. 5, 2011.

* cited by examiner

*Primary Examiner* — Rene Towa
(74) *Attorney, Agent, or Firm* — McDermott Will & Emery LLP

(57) ABSTRACT

The invention provides a biometric apparatus having a display which allows a measured person to recognize biometric data easily and reliably irrespective of whether the measured person is on a platform or not. The biometric apparatus for measuring biometric data of the measured person includes the platform on which the measured person gets on, a sensor unit for acquiring the biometric data of the measured person; a display for displaying the biometric data acquired by the sensor unit; and a control unit for determining whether the measured person is on the platform or not on the basis of a signal from the sensor unit and changes the display mode to display the biometric data on the display according to the determination thereof.

20 Claims, 5 Drawing Sheets

BIOMETRIC APPARATUS

BACKGROUND OF THE INVENTION

1. Field of the Invention

The present invention relates to a biometric apparatus for measuring biometric data and, more specifically, to a biometric apparatus providing good visibility of display of the biometric data.

2. Description of the Related Art

In the related art, various biometric apparatuses for measuring biometric data such as the weight, the percent body fat and the amount of body fat of a measured person have been used. For example, a body-fat-meter-integrated weighting machine is widely used at home as one of the biometric apparatuses. The general body-fat-meter-integrated weighting machine is integrally provided with a display for displaying the results of measurement on a platform as a main body thereof. When the measured person gets on the platform, the weighting machine measures the weight and, in addition, flows a weak constant current from the feet or the hands of the measured person to measure an electric resistance (bioimpedance), and the biometric data such as the percent body fat and the amount of body fat which indicate the composition of internal tissues are measured (JP-A-10-179536). With the body-fat-meter-integrated weighting machine, the results of measurement such as the weight and the body fat are displayed generally in the display provided on the platform. Since the measured person is standing upright on the platform during measurement, the display is at a certain distance from the eyes of the measured person.

However, with the body-fat-meter-integrated weighting machine in the related art, the size of characters showing the results of measurement is the same irrespective of whether the measured person is standing on the platform or has got off the platform. Therefore, even the characters having the size which are easily visible in the state of having got off the platform, they are sometimes hard to read in the state of standing upright on the platform.

When displaying a plurality of biometric data in the display, all the biometric data are displayed simultaneously by reducing the characters which indicate the measured values to a relatively small size. In such a case, the measured person is obliged to bend down toward the display to bring his/her eyes near the display. However, when the measured person is aged of handicapped, he/she may have difficulty to bend his/her body down.

In contrast, when the biometric data is displayed with the characters having a size which allows the measured person to recognize easily in the state of standing upright on the platform, it gives an unpleasant feeling to the measured person such that the characters are too large for the distance from the display to his/her eyes when he/she gets off the platform. In addition when there are a plurality of biometric data to be displayed, the number of the biometric data which can be displayed in the display once due to the limit of the dimensions of the display so that the convenience might be deteriorated for the measured person.

SUMMARY OF THE INVENTION

In view of such problems shown above, it is an object of the invention to provide a biometric apparatus provided with a display which allows measured persons to recognize biometric data easily and reliably irrespective of whether the measured person is on the platform of the biometric apparatus or not.

In order to solve the problems described above, there is provided a biometric apparatus including: a platform on which a measured person gets on; a sensor unit for acquiring the biometric data of the measured person; a display for displaying the biometric data acquired by the sensor unit; and a control unit for determining whether the measured person is on the platform or not on the basis of a signal from the sensor unit and changing a display mode for displaying the biometric data on the display according to the determination thereof.

Preferably, characters indicating the biometric data displayed on the display when the control unit determines that the measured person is on the platform are larger than characters indicating the biometric data displayed on the display when the control unit determines that the measured person is not on the platform.

Preferably, in a case in which a plurality of biometric data are measurable, one of the plurality of biometric data is displayed on the display when the control unit determines that the measured person is on the platform, and the plurality of biometric data are displayed on the display when the control unit determines that the measured person is not on the platform.

Preferably, the plurality of biometric data are displayed sequentially on the display one by one when the control unit determines that the measured person is on the platform.

Preferably, the biometric data to be displayed on the display includes at least one of the weight, the degree of fatness, the percent body fat, the amount of subcutaneous fat, the amount of offal fat and the body age.

Preferably, the display is a full dot liquid crystal display.

Preferably, the sensor unit is a weight sensor provided on the platform for measuring the weight of the measured person.

Preferably, the sensor unit includes electrodes provided on the platform so as to come into contact with the bottom of the feet of the measured person for measuring the bioimpedance of the measured person.

Preferably, the display is fixedly provided on the platform.

Preferably, the display is removably mounted to the platform.

According to the invention, since the display mode of the display is automatically changed according to the state of usage by the measured person, the measured person is able to view the biometric data easily and reliably irrespective of whether he/she is on the biometric apparatus or not.

DESCRIPTION OF THE PREFERRED EMBODIMENTS

Figure 1:
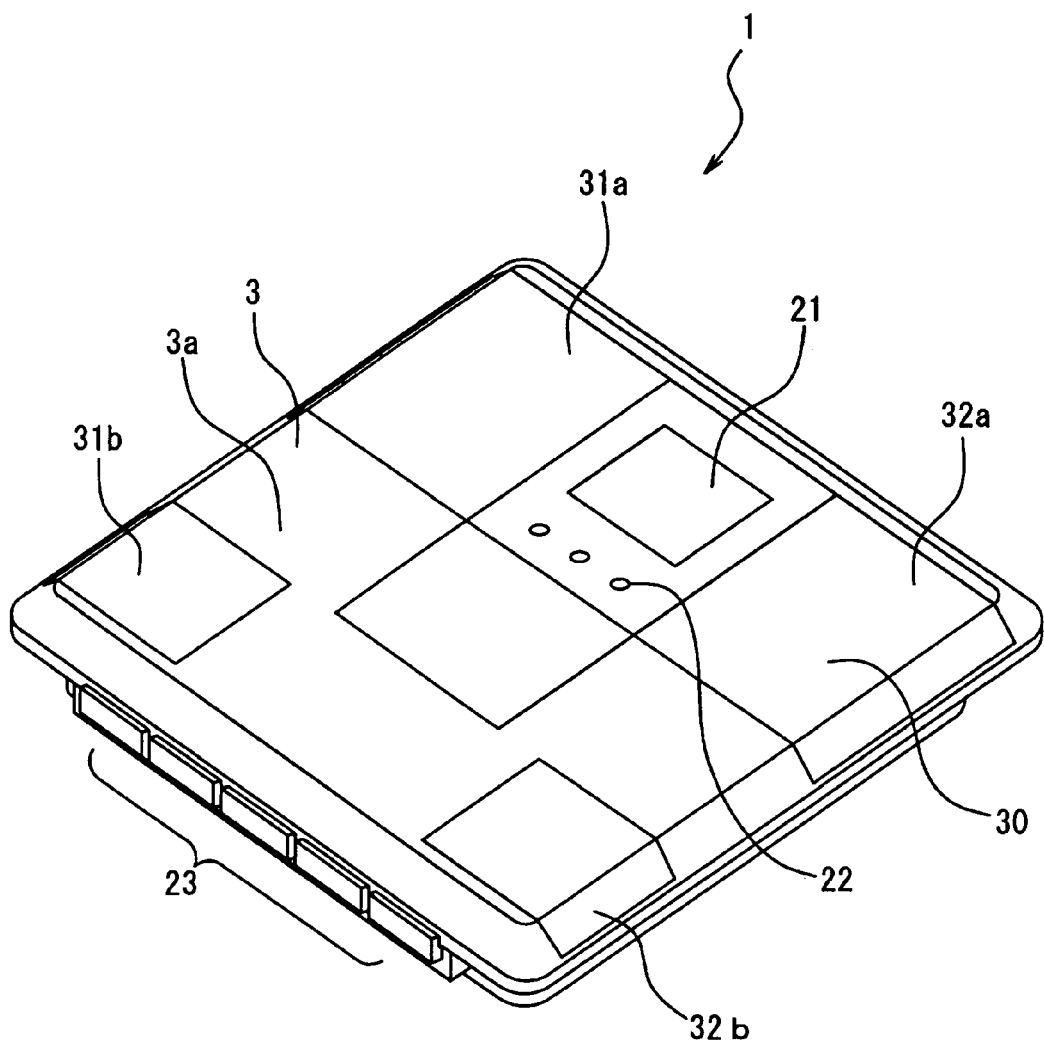
FIG. 1 is a perspective view of a body-fat-meter-integrated weighting machine according to a first embodiment of the invention.
Figure 2:
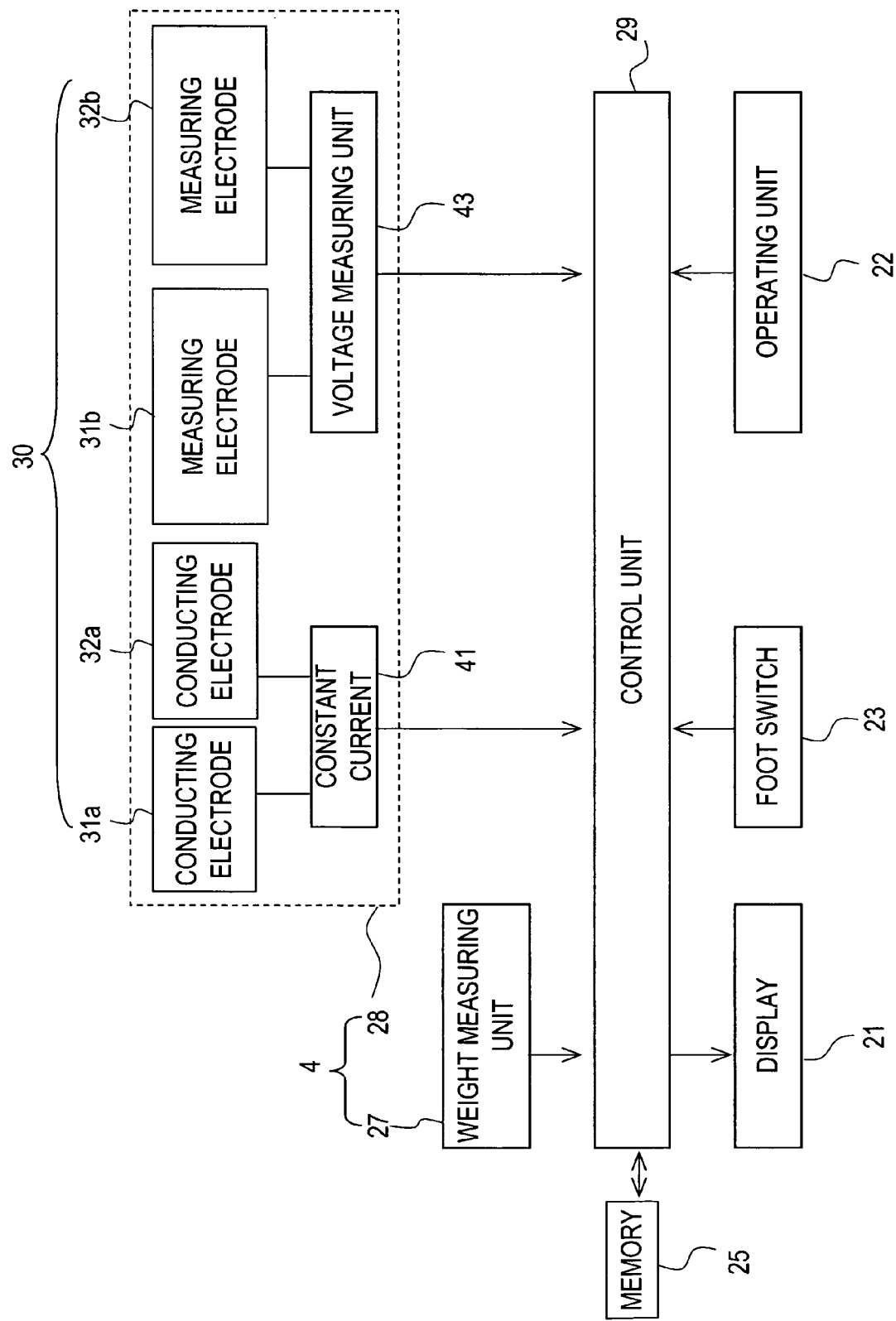
FIG. 2 is a block diagram of the body-fat-meter-integrated weighting machine shown in FIG. 1.
Figure 3:
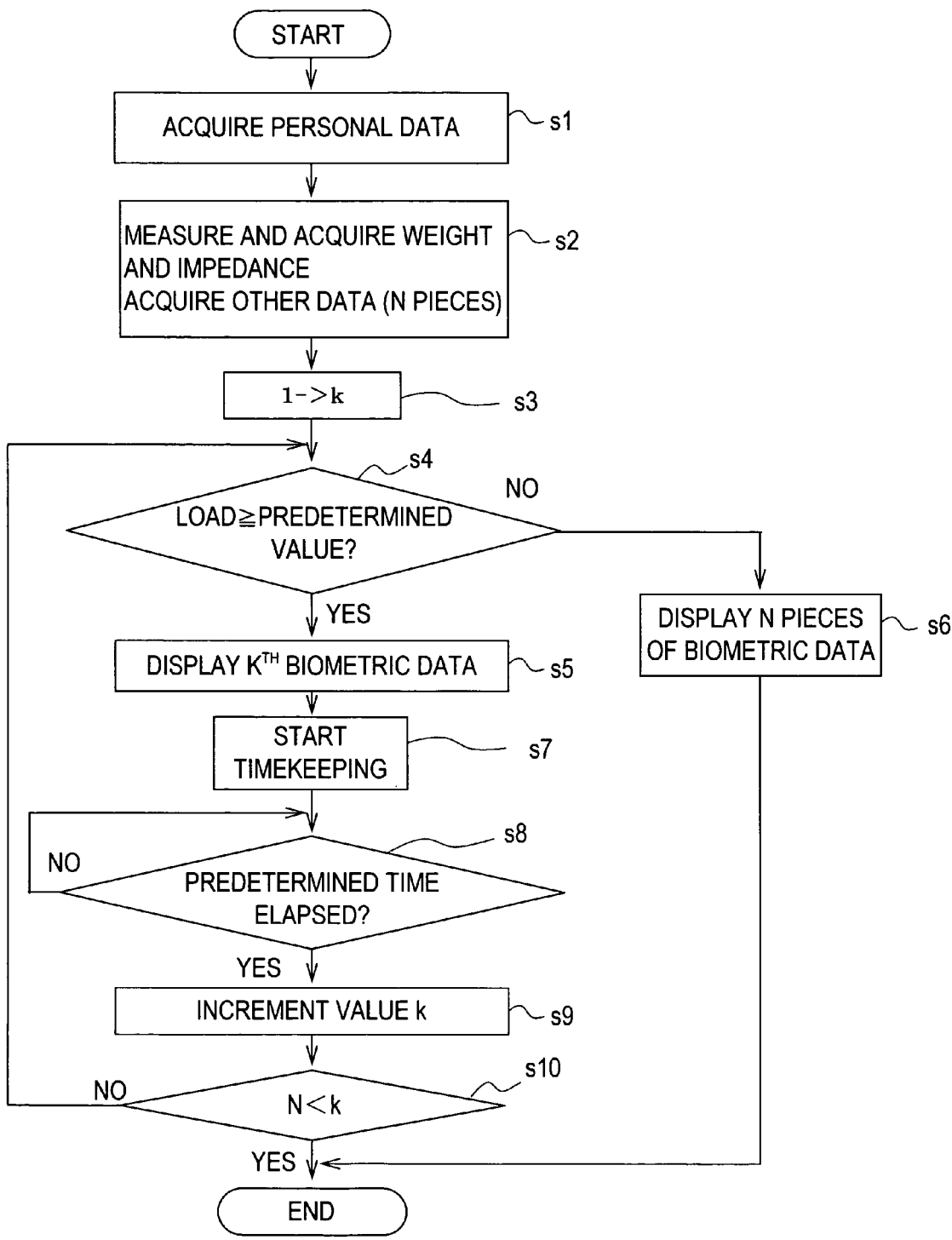
FIG. 3 is a flowchart of a control system of the body-fat-meter-integrated weighting machine shown in FIG. 1.
Figures 4A, 4B:
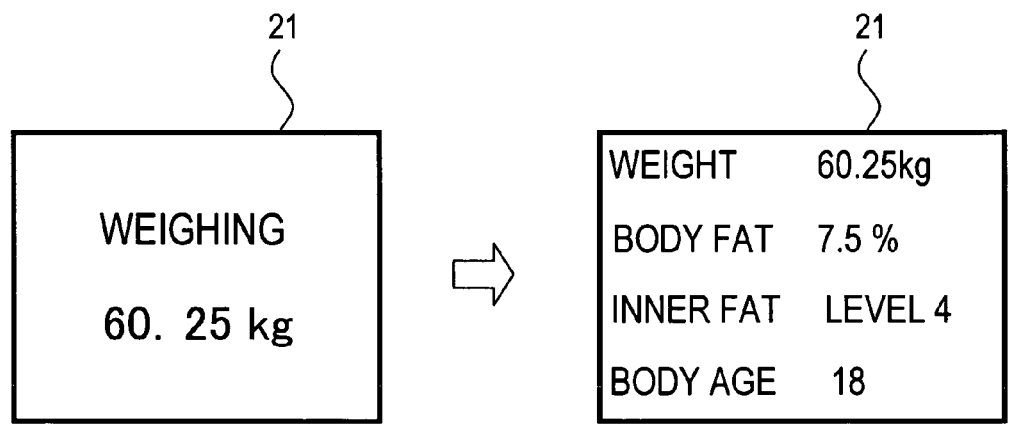
FIG. 4A is an enlarged view of a display of the weighting machine in FIG. 1 showing a display mode of the display in a case in which a control unit determines that a measured person is on a platform.
FIG. 4B is an enlarged view of the display of the weighting machine in FIG. 1 sowing the display mode of the display in a case in which the control unit determines that the measured person is not on the platform.

Referring now to the drawings, a first embodiment in which a biometric apparatus according to the invention is applied to a body-fat-meter-integrated weighting machine will be described. FIG. 1 is a perspective view of a body-fat-meter-integrated weighting machine according to the first embodiment; FIG. 2 is a block diagram of the weighing machine shown in FIG. 1; FIG. 3 is a flowchart of a control system in the body-fat-meter-integrated weighting machine in FIG. 1; FIGS. 4A and 4B are enlarged views of the display of the weighting machine shown in FIG. 1, in which FIG. 4A shows a display mode of the display when it is determined that a measured person is on a platform by a control unit and FIG. 4B shows a display mode of the display when it is determined that the measured person is not on the platform by the control unit.

As shown in FIG. 1 and FIG. 2, a body-fat-meter-integrated weighing machine 1 mainly includes a substantially box-shaped platform 3 on which the measured person gets on, a sensor unit 4 for acquiring biometric data of the measured person, a display 21 provided integrally with the platform 3 for displaying the biometric data acquired by the sensor unit 4, and a control unit 29 for determining whether the measured person is on the platform 3 or not on the basis of a signal from the sensor unit 4 and switches the biometric data to be displayed on the display 21 according to the determination.

The platform 3 is preferably formed of a material such as ABS resin (acrylonitril/butadiene/styrene copolymer). The platform 3 is provided with four thin-plate shaped electrode members 30 arranged so as to be apart from each other on an upper surface 3a thereof. The upper surface 3a of the platform 3 is also provided with the display 21 and an operating unit 22. The display 21 is preferably employs a full dot LCD (Liquid Crystal Display) fixed to the platform 3. However, means which is capable of flexibly displaying various display contents may be selected as needed.

As shown in FIG. 2, the sensor unit 4 of the body-fat-meter-integrated weighting machine 1 according to the first embodiment includes a weight measuring unit 27 for measuring the weight of the measured person and a bioimpedance measuring unit 28 for measuring the percent body fat of the measured person. The weight measuring unit 27 is configured, for example, as a load cell including a distortable member formed of a metallic member which is distorted according to an applied load and a strain gauge attached to the distortable member, and the weight of the measured person is measured by using such mechanism that when the distortable member is bent by the load, the strain gauge expands or contracts, so that the value of resistance of the strain gauge changes.

The bioimpedance measuring unit 28 includes the electrode members 30, a constant current supply unit 41 and a voltage measuring unit 43. The electrode members 30 includes conducting electrodes 31a, 32a and measuring electrodes 31b, 32b, which are to come into contact with feet of the measured person (see FIG. 2).

The operating unit 22 is entry means for entering the personal biometric data such as the height, the sex, and the age or setting items suitable for the individual. The entered personal biometric data or the setting items are stored in a memory 25 or displayed on the display 21. A foot switch 23 is adapted to activate the weighting machine 1 and to read out the personal biometric data or the setting items if stored in the memory 25 in advance. For example, when a plurality of measured persons uses the weighting machine 1, a plurality of the foot switches 23 are allocated to the measured persons respectively, so that the measured person is able to read out his/her own biometric data or the setting items by pushing the foot switch allocated to him/her.

The setting items in this specification means the setting items necessary when the measured person (user) uses the weighting machine 1. For example, it includes the size of the characters indicating the biometric data to be displayed on the display 21. More specifically, it includes the specific sizes (number of dots) of the characters indicating the biometric data displayed on the display 21 in both cases where the measured person is on the platform 3 and where the measured person is not on the platform 3, the characters displayed in the former case being larger than the characters displayed in the latter case as described later. Alternatively, it may be adapted to be able to set in such a manner as to display only the weight and the percent body fat when the measured person is on the platform 3, and to display all the biometric data when the measured person is not on the platform 3 as another type of display of the biometric data on the display.

Subsequently, the control system of the weighting machine 1 will be described. As shown in FIG. 2, the control unit 29 is electrically connected to the display 21, the operating unit 22, the foot switch 23, the memory (for example, non-volatile memory) 25, the weight measuring unit 27 and the bioimpedance measuring unit 28.

The weight measuring unit 27 sends a signal relating to the weight of the measured person to the control unit 29, and the control unit 29 computes the weight on the basis of the sent signal. The bioimpedance measuring unit 28 includes the constant current supply unit 41 for providing a high-frequency weak constant current, the voltage measuring unit 43 for measuring the potential difference of the living body, the conducting electrodes 31a, 32a connected to the constant current supply unit 41, and the measuring electrodes 31b, 32b connected to the voltage measuring unit 43. In the first embodiment, the pair of the conducting electrode 31a and the measuring electrode 31b are arranged so as to come into contact with the bottom of the left foot, and the pair of the conducting electrode 32a and the measuring electrode 32b are arranged so as to come into contact with the bottom of the right foot. The weak constant current is applied from the constant current supply unit 41 to the left foot and the right foot via the conducting electrodes 31a, 32a respectively to measure the bioimpedance. On the basis of the signal indicating the bioimpedance between both feet acquired by the voltage measuring unit 43 connected to the measuring electrodes 31b, 32b, the control unit 29 computes the percent body fat or the amount of body fat. The percent body fat acquired by computation is displayed on the display 21 or stored in the memory 25.

The control unit 29 connected to the weight measuring unit 27 computes the weight of the measured person on the basis of the output signal from the weight measuring unit 27. The obtained weight is displayed on the display 21 or stored in the memory 25.

Although the control unit 29, the memory 25, the weight measuring unit 27 the constant current supply unit 41 and the voltage measuring unit 43 arranged in the interior of the platform 3 are shown in FIG. 2, they are omitted in FIG. 1.

Referring now to FIG. 3, the control process of the body-fat-meter-integrated weighting machine 1 will be described. When the measured person presses the foot switch 23 and activate the weighting machine 1, the control unit 29 carries out the control process shown in the flowchart in FIG. 3.

First of all, the biometric data such as the height, the age and the sex of the measured person are entered to the control unit 29, and are stored in the memory 25 by the operation of the operating unit 22 by the measured person (Step S1). Then, when the measured person gets on the platform 3, N-pieces of biometric data relating to the measured person, such as the weight, the percent body fat, the amount of body fat, the amount of offal fat and the body age are computed and stored in the memory 25 (Step S2).

Then, in Step S3, the value "1" is substituted as a default value for a variable "k" which indicates the number of times of the process relating to the display on the display 21 carried out by the control unit 29.

In Step S4, whether the load equal to or larger than a predetermined value is applied to the platform 3 or not is determined by the signal from the weight measuring unit 27. When the load equal to or larger than the predetermined value is applied to the platform 3, the control unit 29 determined that the measured person is on the platform 3, and goes to the next Step S5. Only the first biometric data (for example, the weight) is displayed in characters which are relatively large on the display 21 (see FIG. 4A).

On the other hand, when only a load smaller than the predetermined value is applied to the platform 3, it is determined that the measured person have gotten off the platform 3, and the procedure goes to Step S6. In Step S6, a plurality (N) of the biometric data acquired in Step S2 are displayed on the display 21 at once (see FIG. 4B). The display mode in Step S6 is different from the display mode in Step S5. In the first embodiment, the size of the characters indicating the biometric data in Step S6 is set to be smaller than the characters indicating the biometric data in Step S5.

When the control unit 29 determines that the measured person is on the platform 3 in Step S4, the biometric data is displayed in the next Step S5, and the control unit 29 starts timekeeping in Step S7. The time to be kept is time intervals to display one biometric data, and it is set by the measured person as needed. Then, the control unit 29 determines whether the predetermined time is elapsed (time is over) or not (Step S8).

When it is determined that the predetermined time is elapsed after having started the display in Step S5 (Step S8), the procedure goes to Step S9. In Step S9, the control unit 29 increments the variable k which indicates the number of times of the process (that is, k is incremented to 2). Then, the control unit 29 determines whether the variable k is larger than the number of the biometric data (N) or not in the next Step S10. When the variable k is smaller than N, the procedure goes back to Step S4 again, where weather the measured person is on the platform 3 or not is determined. Since the value k is 2 in this case, the procedure goes back to Step S4 again, and whether the measured person is on the platform 3 or not is determined. If yes, the second biometric data different from the currently displayed biometric data (the percentage body fat, for example) is displayed on the display 21 (Step S5). The display mode in display 21 is the same as the display mode of the weight displayed previously in Step S5, and the characters in the larger size than those used in Step S6 are displayed.

After Step S5, the timekeeping is started again (Step S7). Then, as described above, whether the predetermined time is elapsed or not is determined (Step S8) and, if yes, the procedure goes to Step S9, where the control unit 29 increments the variable k (that is, the value k is incremented to 3). Then, the procedure goes back to Step S4 again, where the next (third) biometric data (for example, the amount of offal fat) is displayed by the characters in the large size. In this manner, according to the first embodiment, when the measured person is on the platform 3, the control unit 29 repeats the process until the number of times of process reaches N, and the biometric data is displayed one by one on the display. When the measured person has gotten off the platform 3, all the N biometric data are displayed thereon.

According to the first embodiment, the control unit 29 determines whether the measured person is on the platform 3 or has gotten off the platform 3 on the basis of the data from the body weight measuring unit 27. However, the invention is not limited to this configuration, and determination on the basis of data from other mean is also possible. For example, the control unit 29 may be adapted to determine whether the measured person is on the platform 3 or not on the basis of the signal from the bioimpedance measuring unit 28. In this case, the control unit 29 is adapted to determine that the measured person is on the platform 3 when the percent body fat computed by the control unit 29 on the basis of the signal indicating the bioimpedance as an output from the bioimpedance measuring unit 28 is within a predetermined range above and below the value of BMI (Body Mass Index) obtained by squaring the weight value (kg)/height (m), and determine that the measured person has gotten off the platform 3 when the percentage is out of this range.

As described thus far, according to the configuration in the first embodiment, the display mode for displaying the biometric data on the display is automatically changed by determining whether the measured person is on the platform 3 or the measured person has gotten off the platform 3. Therefore, the measured person is able to view the biometric data on the display reliably and easily, so that the user friendly weighting machine is provided. More specifically, when the measured person is on the platform, since the characters displayed on the display is large, the measured person is able to view the biometric data easily and reliably. When the measured person has gotten off the platform, the measured person is able to change the distance form his/her eyes to the display freely, the biometric data can be viewed reliably and easily even when the plurality of biometric data are displayed at once in small characters. Therefore, the measured person is able to know a number of biometric data at once, and the highly convenience weighting machine is provided.

In this manner, according to the configuration in the first embodiment, the plurality of biometric data are acquired. However, the invention may be applied even in the case of the weighting machine for measuring only the weight of the measured person as a single biometric data as a matter of course. In this case, after having acquired the weight, the weight is displayed using large characters on the display 21 in Step S3. The timekeeping starts in Step S4, and the control unit 29 determines whether the load applied to the platform 3 is equal to or larger than the predetermined value in Step S5. When the load is equal to or larger than the predetermine value, the display of the weight in large characters are maintained. When the load is smaller than the predetermined value, the procedure goes to Step S7, and displays in characters smaller than those used in Step S3. Therefore, there is provided the weighting machine having the display which always provides good visibility to the measured person irrespective of whether the measured person is on the weighting machine or not.

In the first embodiment, determination whether the measured person is on the platform 3 or not is not carried out until the predetermined time has elapsed (Step S8) from the start of timekeeping (Step S7). However, a process of determining whether the load is applied or not within a predetermined time from the start of timekeeping may be added.

Figure 5:
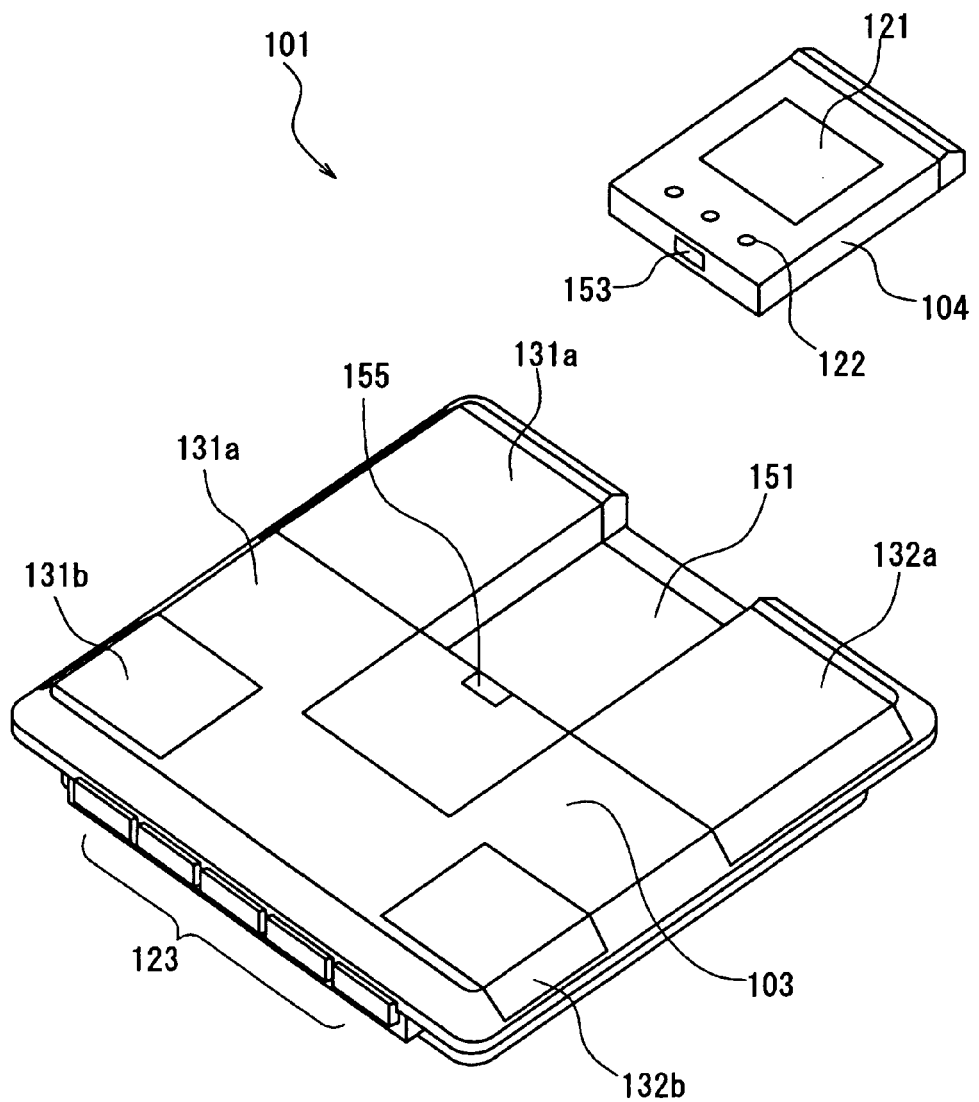
FIG. 5 is a perspective view of a body-fat-meter-integrated weighting machine according to a second embodiment.

Referring now to FIG. 5, a body-fat-meter-integrated weighting machine 101 according to a second embodiment of the invention will be described. FIG. 5 is a perspective view of the body-fat-meter-integrated weighting machine 101 according to the second embodiment. As shown in FIG. 5, the body-fat-meter-integrated weighting machine according to the second embodiment is different from the first embodiment in that a display unit 104 having a display 121 is removably mounted to a platform 103. Therefore, as regards the configuration and function of the body-fat-meter-integrated weighting machine according to the second embodiment, only the points different from the weighting machine 1 according to the first embodiment will be mainly described, and detail description of the same components as in the first embodiment will be omitted.

The body-fat-meter-integrated weighting machine 101 includes a platform 103 as a main body thereof, and a display unit 104 which is removably mounted to the platform 103. The platform 103 is provided with a storage 151 at the upper center portion in the drawing. The storage 151 is a recess notched in a shape complementary to the shape of the display unit 104 so as to store the display unit 104. The weighting machine 101 is also provided with a communication unit 155 in the vicinity of the storage 151 of the platform 103 as communicating means with respect to the display unit 104. The weighting machine 101 is provided with foot switches 123 on the side of the platform 103. In the interior of the platform, the control unit, the weight measuring unit, and the bioimpedance measuring unit are provided. In the configuration described above, the biometric data acquired by the platform is transferred to the display unit 104 via the communication unit 155 by the instruction from the control unit. The functions of the individual components are the same as in the first embodiment, and hence description will be omitted.

The display unit 104 includes the display 121 composed of a full-dot LCD, an operating unit 122, a communicating unit 153 which enables communication with the platform 103, the control unit electrically connected to the display 121, the operating unit 122 and the communicating unit 153, and the memory for storing the biometric data or the like. The display unit 104 and the platform 103 are communicable with each other by communicating means such as infrared ray signal or the like via the respective communication unit 155, 153. Transmission of data between the display unit 104 and the platform 103 may be configured be done via a line instead of wireless, as a matter of course.

The operation of the body-fat-meter-integrated weighting machine 101 in the configuration as described above is the same as in the first embodiment. The different point is that the signals from the weight measuring unit and the bioimpedance measuring unit are used for computing the weight and the percentage body fat by the control unit of the platform 103, and the computed data is transferred to the display unit 104 via the communicating units 153, 155 and is displayed on the display 121. The display mode of the display 121 is the same as those described in conjunction with FIG. 3 and FIG. 4.

As described thus far, according to the body-fat-meter-integrated weighting machine 101 in the second embodiment of the invention, the display unit 104 is removable, which is different from the first embodiment. Therefore, by putting the display unit 104 at a position which is easily viewable from the measured person, the measured person is able to view the display 121 of the display unit 104 at a desired distance even when he/she is standing upright on the platform 103, and hence it satisfies needs of more measured persons with one single weighting machine. For example, the user having general eyesight may use the weighting machine in a state in which the display unit 104 is mounted to the platform 103. In contrast, when the user having poor eyesight uses the weighting machine 101, the display unit 104 may be placed at a position where the user can easily view. In addition, since the biometric data shown in the display 121 is displayed with large characters while the measured person is on the weighting machine 101, easier and more reliable recognition is ensured.

In the first embodiment and the second embodiment, the next biometric data is displayed (Step S5) after having elapsed the predetermined time period (Step S8) after having started the timekeeping (Step S7). However, Step S7 and Step S8 are not essential elements of the invention.

In the first embodiment and the second embodiment, the bioimpedance between both feet is measured for measuring the percent body fat. However, a configuration to measure the bioimpedance between hands or a combination of these configurations is also applicable.

In the embodiments shown above, description is made assuming that the plurality (N) of biometric data are displayed on the display 21 at once when the measured person is not on the platform 3. However, the biometric data may be displayed sequentially in numbers, such as to display by N/2 biometric data considering the visibility of the display and the relation of the biometric data.

In the embodiments shown above, the size of the characters indicated on the display is changed depending on whether the measured person is on the platform 3 or not. However, the size of signs or marks indicating the biometric data as well as the size of the characters may be changed for display.

In the embodiment shown above, the size of the characters and the number of biometric data to be displayed on the display are changed depending on the case in which the load is applied to the weighting machine and the case in which the load is not applied thereto. However, various other modes are also applicable. For example, a configuration to display only the biometric data obtained at the time of measurement when the measured person is on the biometric apparatus, and read out and display other biometric data measured in the past and stored when the measured person has gotten off the biometric apparatus, or a configuration to display a graph created by plotting the plurality of biometric data obtained in the past and the latest biometric data is also applicable.

In the first embodiment and the second embodiment, the load cell is used as the weight sensor. However, various means such as a electromagnetically balancing weight measuring apparatus configured to apply an electromagnetic force as a sensor in the invention and measuring the weight from the amount of electricity thereof, or a measuring apparatus having a pressure sensor using the piezoelectric crystal may also be applied.

The invention may be implemented in various modes without departing from its essential features. Therefore, it is needless to say that the embodiments described above are illustrative only, and do not limit the invention.

What is claimed is:

1. A biometric apparatus for measuring body composition data of a measured person comprising:
   a platform on which the measured person gets on;
   a sensor unit for acquiring the body composition data of the measured person and outputting a signal indicating a status of whether the measured person is on or off the platform;
   a display for displaying the body composition data acquired by the sensor unit; and
   a control unit for determining, after having acquired the body composition data of the measured person, whether or not the measured person is still on the platform on the basis of the signal from the sensor unit, and displaying the acquired body composition data on the display in one of different manners according to the determination thereof, wherein:

when the control unit determines that the measured person is still on the platform, the control unit causes the display to display the acquired body composition data in one of the different manners based on the signal received from the sensor unit, and, when the control unit determines that the measured person is not on the platform, the control unit causes the display to display the acquired body composition data in another one of the different manners based on the signal received from the sensor unit, wherein characters indicating the acquired body composition data displayed on the display are larger in the one of the different manners than characters indicating the acquired body composition data displayed on the display in the another one of the different manners, and wherein the control unit switches between the different manners in response to the signal indicating that said status has changed.

2. The biometric apparatus according to claim 1, wherein:
the body composition data includes a plurality of types of body composition data, and
the control unit displays the acquired body composition data in the one of different manners such that at least one, but not all, of the plurality of types of body composition data is displayed on the display when the control unit determines that the measured person is still on the platform, and all of the plurality of types of body composition data are displayed on the display when the control unit determines that the measured person is not on the platform.

3. The biometric apparatus according to claim 1, wherein:
the body composition data includes a plurality of types of body composition data, and
the control unit displays the acquired body composition data in the one of different manners such that all of the plurality of types of body composition data are displayed sequentially on the display one by one when the control unit determines that the measured person is on the platform.

4. The biometric apparatus according to claim 1, wherein the body composition data to be displayed on the display includes at least one of the weight, the degree of fatness, the percent body fat, the amount of subcutaneous fat, the amount of offal fat and the body age.

5. The biometric apparatus according to claim 1, wherein the display is a full dot liquid crystal display.

6. The biometric apparatus according to claim 1, wherein the sensor unit is a weight sensor provided on the platform for measuring the weight of the measured person.

7. The biometric apparatus according to claim 1, wherein the sensor unit includes electrodes provided on the platform so as to come into contact with the bottom of the feet of the measured person for measuring a bioimpedance of the measured person.

8. The biometric apparatus according to claim 1, wherein the display is fixedly provided on the platform.

9. The biometric apparatus according to claim 1, wherein the display is removably mounted to the platform.

10. The biometric apparatus according to claim 1, wherein past body composition data measured prior to measuring the body composition data are displayed on the display when the control unit determines that the measured person is not on the platform.

11. A biometric apparatus for measuring body composition data of a measured person comprising:
a platform on which the measured person gets on;
a sensor unit for acquiring the body composition data of the measured person and outputting a signal indicating a status of whether the measured person is on or off the platform;
a display for displaying the body composition data acquired by the sensor unit; and
a control unit for determining, after having acquired the body composition data of the measured person, whether or not the measured person is still on the platform on the basis of the signal from the sensor unit, and displaying the acquired body composition data on the display in one of different manners according to the determination thereof, wherein:

when the control unit determines that the measured person is still on the platform, the control unit causes the display to display the acquired body composition data in one of the different manners based on the signal received from the sensor unit, and, when the control unit determines that the measured person is not on the platform, the control unit causes the display to display the acquired body composition data in another one of the different manners based on the signal received from the sensor unit, the body composition data includes a plurality of types of body composition data, wherein in the one of the different manners a number of types of body composition data displayed on the display is smaller than a number of types of body composition data displayed on the display in the another one of the different manners, and wherein the control unit switches between the different manners in response to the signal indicating that said status has changed.

12. The biometric apparatus according to claim 11, wherein the body composition data to be displayed on the display includes at least one of the weight, the degree of fatness, the percent body fat, the amount of subcutaneous fat, the amount of offal fat and the body age.

13. The biometric apparatus according to claim 11, wherein the display is a full dot liquid crystal display.

14. The biometric apparatus according to claim 11, wherein the sensor unit is a weight sensor provided on the platform for measuring the weight of the measured person.

15. The biometric apparatus according to claim 11, wherein the sensor unit includes electrodes provided on the platform so as to come into contact with the bottom of the feet of the measured person for measuring a bioimpedance of the measured person.

16. The biometric apparatus according to claim 11, wherein the display is fixedly provided on the platform.

17. The biometric apparatus according to claim 11, wherein the display is removably mounted to the platform.

18. The biometric apparatus according to claim 11, wherein all of the plurality of types of body composition data are displayed on the display when the control unit determines that the measured person is not on the platform.

19. The biometric apparatus according to claim 11, wherein past body composition data measured prior to measuring the body composition data are displayed on the display when the control unit determines that the measured person is not on the platform.

20. The biometric apparatus according to claim 11, wherein only one of the types of body composition data is displayed on the display when the control unit determines that the measured person is still on the platform, and two or more of types of body composition data are displayed on the display when the control unit determines that the measured person is not on the platform.

* * * * *